US012594328B2

(12) United States Patent　　　　(10) Patent No.:　US 12,594,328 B2
Witvliet et al.　　　　　　　　　　　(45) Date of Patent:　　　Apr. 7, 2026

(54) COMBINATION OF VACCINES TO PROPHYLACTICALLY TREAT A PIG

(71) Applicant: Intervet Inc., Madison, NJ (US)

(72) Inventors: Maarten Hendrik Witvliet, Oostrum (NL); Jacquelyn Horsington, Nijmegen (NL)

(73) Assignee: Intervet Inc., Rahway, NJ (US)

( * ) Notice: Subject to any disclaimer, the term of this patent is extended or adjusted under 35 U.S.C. 154(b) by 772 days.

(21) Appl. No.: 17/918,006

(22) PCT Filed: Apr. 19, 2021

(86) PCT No.: PCT/EP2021/060015
§ 371 (c)(1),
(2) Date: Oct. 10, 2022

(87) PCT Pub. No.: WO2021/213949
PCT Pub. Date: Oct. 28, 2021

(65) Prior Publication Data
US 2023/0338500 A1　　Oct. 26, 2023

(30) Foreign Application Priority Data

Apr. 20, 2020　(EP) ..................................... 20170442

(51) Int. Cl.
*A61K 39/12*　　　(2006.01)
*A61K 39/00*　　　(2006.01)
*A61K 39/02*　　　(2006.01)
*A61K 39/295*　　(2006.01)
*A61P 31/04*　　　(2006.01)
*A61P 31/20*　　　(2006.01)
*C12N 7/00*　　　(2006.01)

(52) U.S. Cl.
CPC .......... *A61K 39/12* (2013.01); *A61K 39/0241* (2013.01); *A61K 39/295* (2013.01); *A61P 31/04* (2018.01); *A61P 31/20* (2018.01); *C12N 7/00* (2013.01); *A61K 2039/522* (2013.01); *A61K 2039/5254* (2013.01); *A61K 2039/54* (2013.01); *A61K 2039/545* (2013.01); *A61K 2039/552* (2013.01); *A61K 2039/70* (2013.01); *C12N 2750/00022* (2013.01); *C12N 2750/10021* (2013.01); *C12N 2750/10034* (2013.01); *C12N 2750/10062* (2013.01); *C12N 2750/10071* (2013.01)

(58) Field of Classification Search
None
See application file for complete search history.

(56) References Cited

U.S. PATENT DOCUMENTS

2020/0046825 A1　　2/2020　Witvliet et al.

FOREIGN PATENT DOCUMENTS

| JP | 2017523139 A | 8/2017 |
|---|---|---|
| JP | 2019509300 A | 4/2019 |
| WO | 2015189425 A1 | 12/2015 |
| WO | 2017162741 A1 | 9/2017 |
| WO | 2018189290 A1 | 10/2018 |

OTHER PUBLICATIONS

Nakano, Takashi, Hearing on the PDCA Cycle in the Basic Plan for Vaccinations: 'Simultaneous Administration and Administration Intervals', 18th Meeting of the Health Sciences Council, N/A, Slide 14, 2017 (English translation).

Charerntantanakul, Wasin et al., Co-administration of saponin quil A and PRRSV-1 modified-live virus vaccine up-regulates gene expression of type I interferon-regulated gene, type I and II interferon, and inflammatory cytokines and reduces viremia in response to PRRSV-2 challenge, Veterinary Immunology and Immunopathology, 205, 24-34, 2018.

Dolan, Samantha B. et al., Administering Multiple Injectable Vaccines During a Single Visit—Summary of Findings From the Accelerated Introduction of Inactivated Polio Vaccine Globally, The Journal of Infectious Diseases, 216 (Suppl 1), S152-S160, 2017.

Kharkevich, D.A., Pharmacology, Moscow: GEOTAR-Media, 10th Edition, 73-74, 2010.

Kharkevich, D.A., Pharmacology, Moscow: GEOTAR-Media, Textbook for HS, 10th Ed., 73-74, 2010.

Oh, Taehwan et al., Evaluation of the efficacy of a trivalent vaccine mixture against a triple challenge with Mycoplasma hyopneumoniae, PCV2, and PRRSV and the efficacy comparison of the respective monovalent vaccines against a single challenge, BMC Veterinary Research, 15:342, 1-12, 2019.

Svistunov, A.A., et al., Pharmacology: Textbook, M.: Laboratory of Knowledge, N/A, 55-56, 2017.

Department Of Health: "Immunization Program", Dec. 1, 2018 (Dec. 1, 2018), XP055732044, Retrieved from the Internet: URL: https ://www. health.state.mn.us/people/immunize/hcp/admim. pdf[retrieved on Sep. 18, 2020], 2 pages.

Dolan, Samantha et al., Summary of evidence on the administration of multiple injectable vaccines in infants during a single visit: safety, immunogenicity, and vaccine administration practices, Apr. 2015 SAGE Meeting, 2015, 1-44, N/A.

(Continued)

*Primary Examiner* — Daniel C Gamett
(74) *Attorney, Agent, or Firm* — Susanna C. Benn

(57)　　　　　　ABSTRACT

The invention pertains to a combination of a first vaccine comprising a non-replicating immunogen of porcine circovirus type 2 (PCV-2) and a non-replicating immunogen of *Mycoplasma hyopneumoniae*, and a second vaccine comprising a live attenuated porcine reproductive and respiratory syndrome (PRRS) virus, for use in prophylactically treating a pig against an infection with PCV-2, an infection with *Mycoplasma hyopneumoniae* and an infection with PRRS virus, by associated separate injection of the first vaccine and the second vaccine into a tissue of the pig at a first and a second injection site respectively, wherein the first and second injection sites are at most 5 cm apart from each other.

9 Claims, No Drawings

(56) References Cited

OTHER PUBLICATIONS

Ruansit, Wilawan et al., 0ral supplementation of quercetin in PRRSV-1 modified-live virus vaccinated pigs in response to HP-PRRSV-2 challenge, Vaccine, 2020, 3570-3581, 38(19).

Saskatchewan: "Saskatchewan Immunization Manual Chapter 8—Administration of Biological Products", Jun. 1, 2018 (Jun. 1, 2018), XP55732030, Retrieved from the Internet:URL: https://www.ehealthsask.ca/services/Manuals/Documents/sim-chapter8.pdf [retrieved on Sep. 18, 2020], 39 pages.

COMBINATION OF VACCINES TO PROPHYLACTICALLY TREAT A PIG

CROSS-REFERENCE TO RELATED APPLICATIONS

This application is a National Stage application of International Patent Application No. PCT/EP2021/060015, filed Apr. 19, 2021, which claims priority to European Patent Application No. EP 20170442.6, filed Apr. 20, 2020.

GENERAL FIELD OF THE INVENTION

The invention in general pertains to the field of swine (pig) health. Pigs are prone to many pathogenic microorganisms. Control of infection is commonly done by farm and feed management, treatment with pharmaceuticals such as anti-viral drugs and antibiotics, or prophylactic treatment using vaccines. In particular, the invention pertains to vaccines against porcine circovirus type 2 (PCV2 or PCV-2), *Mycoplasma hyopneumoniae*, and porcine reproductive and respiratory syndrome (PRRS) virus, and to a method of protecting an animal against such infections using such vaccines.

BACKGROUND OF THE INVENTION

PCV-2 is linked to the post-weaning multisystemic wasting syndrome (PMWS) observed in young pigs. This disease was encountered for the first time in Canada in 1991. The clinical signs and pathology were first published in 1996, and include progressive wasting, dyspnea, tachypnea, and occasionally icterus and jaundice.
Nayar et al., Can. Vet. J. Volume 38, June 1997 detected PCV in pigs with clinical symptoms of PMWS and concluded that a PCV, other than the known PCV recognized as a natural inhabitant of PK-15 cells, could be linked to PMWS. Later publications (Hamel et al., J. Virol., 72(6), 5262-5267, 1998; Meehan et al., J. Gen. Virol., 79, 2171-2179, 1998) confirmed these findings, and it was proposed (Meehan et al., supra) to refer to the new pathogenic PCV as PCV-2, whereas the original PK-15 cell culture isolate (Tischer et al., Nature 295, 64-66, 1982), should be referred to as PCV-1. PCV-2 is a small (17-22 nm) icosahedral non-enveloped virus containing a circular single-stranded DNA genome. The length of the PCV-2 genome is about 1768 bp. PCV-2 isolates originating from different regions in the world seem to be closely related to each other and display about 95 to 99% nucleotide sequence identities (Fenaux et al., J. Clin. Micorbiol., 38(7), 2494-2503, 2000). ORF2 of PCV encodes the capsid protein of the virus. The ORF2 gene of PCV-2 encodes a protein of about 233 amino acids. The ORF 2 gene of all PCV-2 isolates share 91-100% nucleotide sequence identity and 90-100% deduced amino acid sequence identity.

*Mycoplasma hyopneumoniae* (Mhyo) is a species of bacteria known to cause the disease Porcine Enzootic Pneumonia, a highly contagious and chronic disease affecting pigs. Mhyo is small in size (400-1200 nm), has a small genome (893-920 kilo-base pairs (kb)) and lacks a cell wall. Mhyo attaches to the cilia of epithelial cells in the lungs of swine. They cause cilia to stop beating, clumping and loss of cilia, eventually leading to epithelial cell death. This is the source of the lesions found in the lungs of pigs with porcine enzootic pneumonia. This damage impedes normal ciliary clearance and often secondary infections develop. This causes a significant reduction in the growing weight of the animals. Losses in the U.S.A. have been previously estimated to be up to 1 billion dollars per annum. Porcine enzootic pneumonia is endemic worldwide and Mhyo is present in almost every pig herd. The immune response induced by the presence of Mhyo in pigs is slow and ineffective. Treatment of this disease is therefore of the utmost importance but is limited to antibiotics, which are currently only partly effective as they do not completely remove the infection. Vaccines have been found to reduce the severity of the disease but do not completely prevent the disease from occurring in infected pigs.

PRRS virus was first reported in 1987 in North America and Central Europe. PRRS virus is a small, enveloped RNA virus. It contains a single-stranded, positive-sense, RNA genome with a size of approximately 15 kilobases. The genome contains nine open reading frames. The virus is a member of the genus Arterivirus, family *Arteriviridae*, order Nidovirales. The two prototype strains of PRRSV are the North American strain, VR-2332, and the European strain, the Lelystad virus (LV). The European and North American PRRSV strains cause similar clinical signs. Recently a highly pathogenic strain of the North American genotype emerged in China. This strain, HP-PRRSV, is more virulent than all other strains, and causes great losses in Asian countries. Clinical signs include reproductive failure in sows such as abortions and giving birth to stillborn or mummified foetuses, and cyanosis of the ear and vulva. In neonatal pigs, the disease causes respiratory distress, with increased susceptibility to respiratory infections such as Glässer's disease.

Vaccines against the above identified pathogens are commonly known. A conventional vaccine to prophylactically treat animals, in particular pigs, against an infection with PCV 2, may be based on whole inactivated PCV-2 virus as (non-replicating) immunogen. Also, in the art it has been shown that the ORF2 encoded capsid protein (e.g. when recombinantly expressed) is suitable as a subunit immunogen of PCV-2 for use in an adequate vaccine. This can be understood since this subunit in a circulatory system, presents the same way as the virus itself (it forms virus-like particles), essentially differing only in the fact that the DNA and non-structural proteins are not present inside the capsid. In the art several vaccines against PCV-2 are commercially available. Porcilis® PCV (available from MSD Animal Health, Boxmeer, The Netherlands) is a vaccine for protection of pigs against PCV-2, for use in pigs from three weeks and older. When given as a two-shot (two dose) vaccine, the duration of immunity (DOI) is 22 weeks, almost completely covering the fattening period of pigs. Ingelvac CircoFlex® (available from Boehringer Ingelheim, Ingelheim) is a vaccine for protection of pigs against PCV-2, for use in pigs from two weeks and older. It is registered as a one-shot (one dose) vaccine only. Circovac® (available from Ceva, Libourne, France) is a vaccine for protection of pigs against PCV-2, for use in pigs three weeks and older. Suvaxyn® PCV (available from Zoetis, Capelle a/d Ussel, The Netherlands) is a vaccine for protection of pigs against PCV-2, for use in pigs from three weeks and older. Other PCV-2 vaccines are described for example in WO2007/028823, WO 2007/094893 and WO2008/076915.

Regarding Mhyo, many commercial vaccines exist and these are routinely used in the majority of commercial swine farming operations. Generally these vaccines comprise non-replicating immunogens such as subunit proteins and/or bacterins (i.e. a composition comprising killed bacteria, either as whole cells, (partly) lysed, homogenised, French pressed, a combination of this or comprising the killed bacteria in another form as long as the composition is derived from a killed bacterial culture) which are typically administered by parenteral injection. Some examples are: RespiSure® (Zoetis), Ingelvac® M. hyo, and MycoFLEX® (Boehringer Ingelheim), Hyoresp® (Merial), Stellamune® *Mycoplasma* (Elanco Animal Health), Fostera® PCV MH (Zoetis) and M+Pac® and Porcilis® Mhyo (both available from MSD Animal Health).

Regarding PRRS virus, although inactivated virus vaccines have been described and are commercially available, modified-live vaccines (MLV vaccines) comprising either the European type (type I) or the North American type (type II) in live attenuated form, are the primary immunological tools for its control. Several vaccines are commercially available in the art. Porcilis® PRRS (available from MSD Animal Health, Boxmeer, The Netherlands) is a vaccine comprising live attenuated PRRS virus type I and is registered to reduce infection (viraemia) caused by infection with PRRS virus. Ingelvac PRRS® MLV (available from Boehringer Ingelheim, Ingelheim) is a vaccine that aids in the reduction of disease caused by PRRS virus and which vaccine provides cross protection against strains of different types. Fostera® PRRS (available from Zoetis, Florham Park, New Jersey, USA) is also a MLV vaccine and is registered for protection against both the respiratory and reproductive forms of disease caused by PRRS virus. Yet another PRRS MLV vaccine is PrimePac PRRS (type II) available from Merck Animal Health, Madison, NJ, USA. Other PRRS vaccines are described for example in WO2006/074986, U.S. Pat. No. 8,728,487 and WO2014/048955.

The above vaccines are commonly used as monovalent vaccines, ready-to-use mixtures (such as Porcilis PCV M Hyo), end-user-made mixtures (such as for example Ingelvac 3FLEX) and/or used for associated non-mixed use such as for example known from WO2018/189290.

OBJECT OF THE INVENTION

There is a continuous need for convenient, safe and efficacious means for the management of swine health. In particular, there is a need for convenient, safe and efficacious vaccines that can be used for prophylactic treatment of a pig against an infection with PCV-2, an infection with Mhyo and an infection with PRRS virus, leading to adequate protection, without severe negative effects of the vaccination process while minimising stress for the vaccinated pig.

SUMMARY OF THE INVENTION

In order to meet the object of the invention it was found that a combination of a first vaccine comprising a non-replicating immunogen of porcine circo virus type 2 (PCV2) and a non-replicating immunogen of *Mycoplasma hyopneumoniae*, and a second vaccine comprising a live attenuated porcine reproductive and respiratory syndrome (PRRS) virus, can be advantageously used in prophylactically treating a pig against an infection with porcine circo virus type 2, an infection with *Mycoplasma hyopneumoniae* and an infection with PRRS virus, by associated separate injection of the first vaccine and the second vaccine into a tissue of the pig at a first and a second injection site respectively, wherein the first and second injection sites are at most 5 cm apart from each other.

Although the associated separate administration of a first vaccine comprising non-replicating immunogen of PCV-2 and non-replicating immunogen of Mhyo, and a second vaccine comprising live attenuated PRRS virus, has been described already in WO2018/189290, it was found that the effects on protection could be even further improved, without introducing any negative side effects, with respect to that disclosure, by injecting the first vaccine and the second vaccine into a tissue of the pig at separate injection sites that lie at most 5 cm apart from each other. Without being bound to theory, it is believed that the injection in close proximity stimulates the immune response in some way or another, potentially by an increased local presence of the antigens as used in the claimed combination, i.e. non-replicating immunogen of PCV-2 and Mhyo, and live attenuated PRRS virus. The increased local presence of the antigen seems to lead to an improved efficacy of the individual vaccines, or at least not a diminished efficacy, without inducing any unwanted side effects. Although typically, a deposition area in pig tissue (such as muscle tissue) after injection may be up to 3-4 cm, and thus, when the two separate vaccines would be injected 6-7 cm apart, there would still be overlap in deposition area and thus, a stimulating effect would be expected, it is believed that when the distance between the injection sites is above 5 cm, the overlap in deposition area of the respective vaccines is so low that no practical advantages remain.

The invention also pertains to a kit-of-parts comprising a first vaccine comprising a non-replicating immunogen of porcine circo virus type 2 (PCV2) and a non-replicating immunogen of *Mycoplasma hyopneumoniae*, and separately a second vaccine comprising a live attenuated PRRS virus, for use in prophylactically treating a pig against an infection with porcine circo virus type 2, an infection with *Mycoplasma hyopneumoniae* and an infection with PRRS virus, by associated separate injection of the first vaccine and the second vaccine into a tissue of the pig at a first and a second injection site respectively, wherein the first and second injection sites are at most 5 cm apart from each other.

The invention is also embodied in a method of prophylactically treating a pig against an infection with porcine circovirus type 2 (PCV2), an infection with *Mycoplasma hyopneumoniae* and an infection with PRRS virus by associated separate injection of the first vaccine and the second vaccine into a tissue of the pig at a first and a second injection site respectively, wherein the first and second injection sites are at most 5 cm apart from each other.

Definitions

A vaccine is a pharmaceutical composition that is safe to administer to a subject animal, and is able to induce protective immunity in that animal against a pathogenic microorganism, i.e. to induce a successful prophylactic treatment as defined here below.

A combination of a first and second vaccine is a set of vaccines, wherein the first vaccine is individually distinct from the second vaccine, but wherein the two vaccines are used in conjunction for administration to the same subject in one concerted treatment.

Non-replicating immunogen of a pathogen is any substance or compound corresponding to the pathogen, other than the live replicating pathogen as a whole (either in wild type of attenuated form), against which pathogen an immunological response is to be elicited, such that the corresponding virulent pathogen or one or more of its virulence factors will be recognized by the host's immune system as a result of this immune response and are ultimately at least partly neutralized. Typical examples of non-replicating immunogens are killed whole pathogens (which term includes these pathogens in lysed form) and subunits of these pathogens such as capsid proteins, surface expressed molecules (for example recombinantly expressed proteins or lipopolysaccharides) and excreted molecules such as toxins.

A bacterin is a suspension of killed bacteria, either as whole cells, partly lysed or completely lysed (such as for example by homogenisation, French pressing, or a combination of two or more lysing methods).

A live attenuated pathogen is a viable, replication competent form of the pathogen having reduced virulence. The process of attenuation takes an infectious pathogen and alters it so that it becomes harmless or less virulent, typically by either multiple passages of the pathogen through cell systems or by genetically modifying the pathogen.

Prophylactic treatment against an infection with a pathogen is aiding in preventing, ameliorating or curing an infection with that pathogen or a disorder arising from that infection, resulting from a post treatment challenge with the pathogenic pathogen, in particular to reduce its load in the host after such challenge or to aid in preventing or ameliorating one or more clinical manifestations resulting from the post treatment infection with the pathogen.

A pig is an animal belonging to the family of Suidae, a family of artiodactyl mammals which are commonly called pigs, hogs or boars. Eight-teen extant species are currently recognized (or nineteen counting domestic pigs and wild boars separately), classified into between four and eight genera. Within this family, the genus *Sus* includes the domestic pig, *Sus scrofa domesticus* or *Sus domesticus.*

Associated administration of vaccines, also referred to as concurrent administration, is the administration of these vaccines separately, thus not mixed before administration, to the target animal, but within a time frame such that immunological interference is expected to occur, typically within 24 hours. Examples of associated use are the simultaneous administration at separate application sites in the target animal, and the administration at the same or separate application sites but at different times, typically separated by 1-6 hours.

Simultaneous administration of vaccines means the administration at exactly the same time or at least within a time frame of 1 hour, preferably within 55, 50, 45, 40, 35, 30, 25, 20, 19, 18, 17, 16, 15, 14, 13, 12, 11, 10, 9, 8, 7, 6, 5, 4, 3, 2 minutes or even a time frame of 1 minute.

Single dose administration of a vaccine for use in prophylactically treatment means that in order to arrive at protective immunity, the vaccination does not need to be boosted with a second administration of the vaccine. In a two-shot regime, the first (prime) vaccination is typically boosted within 6 weeks from the first administration, commonly within 3 or even 2 weeks from the first administration, and only after the second (boost) administration protective immunity, i.e. a successful prophylactic treatment as defined here above, may be obtained.

EMBODIMENTS OF THE INVENTION

In an embodiment of the combination of a first and a second vaccine for use according to the invention, the first and second injection sites are at most 4 cm apart from each other, or at most 3 cm apart from each other. It is believed that the closer proximity of the injections leads to a further increase of the found stimulating effects.

In another embodiment of the combination of a first and a second vaccine for use according to any of the preceding claims, characterised in that the associated separate injection of the first vaccine and the second vaccine occur simultaneously. This embodiment has the advantage that an animal needs to be handled only once, or at least during only a very short timeframe, for depositing both the vaccines in close proximity.

In yet another embodiment the first and second vaccine through the said injection are deposited at least partly into muscular tissue of the pig. The muscular tissue of the pig has found to be particularly advantageous for depositing two separate vaccines in close proximity. The vaccines could be injected for example by using a hypodermic syringe that extends into the muscular tissue or by using a jet stream of the respective vaccines using a needle-less device, wherein the jet stream penetrates the skin of the pig and ultimately reaches the muscle tissue below (not excluding that part of the vaccine is deposited in the dermis).

In still another embodiment the first and second vaccine are administered by a single dose. It was found that a single dose administration of each of the two vaccines led to an effective vaccination against all pathogens. This provides for a very convenient and economical way to protect animals against these pathogens.

In again another embodiment the non-replicating immunogen of PCV-2 is recombinantly expressed protein encoded by the ORF2 gene of PCV-2, such as for example baculovirus expressed protein of PCV-2 as known in the art. This recombinant protein has proven to be suitable for application in the present invention. In particular, the ORF2 protein can be expressed in a baculovirus expression system such as described in WO2007/028823, WO 2007/094893 or WO2008/076915.

In again another embodiment the non-replicating immunogen of *Mycoplasma hyopneumoniae* is a *Mycoplasma hyopneumoniae* bacterin. Such Mhyo antigen is relatively easy to produce and has a good track record of efficacy in the everyday swine industry practice.

The invention will now be explained in more detailed, using the following example.

EXAMPLE

Objective

The objective of this experiment was to determine the efficacy of different mixed and non-mixed combinations of PCV-2, Mhyo and PRRS vaccines in piglets at three weeks of age, determined by PCV2 challenge two weeks post vaccination. PRRS and Mhyo efficacy were evaluated based on serology.

Study Design

Thirty pigs were used for this study. Three groups of 10 animals were vaccinated at the age of three weeks (+/− three days). Group 1 received a single dose of 2 ml of the commercial vaccine Porcilis PCV M Hyo (comprising baculo expressed ORF2 protein of PCV2 and an Mhyo bacterin) applied intramuscularly with a hypodermic syringe in the right side of neck, and a single dose of 2 ml the commercial vaccine Porcilis PRRS (comprising live attenuated PRRS virus, type I) applied intramuscularly with a hypodermic syringe at the same side of the neck, 3 cm apart from the other site of administration. Group 2 received the same vaccinations, but the PCV MHyo vaccine was administered at the right side of the neck, whereas the PRRS vaccine was administered at the left side of the neck. Group 3 was vaccinated with the PRRS vaccine only, serving as the PCV-2 challenge control. At two weeks post vaccination (5 weeks of age) all animals were challenged using a dose of 5.8 $\log_{10}$ $TCID_{50}$ of wild-type PCV-2b challenge virus, applied intranasally.

Three weeks post challenge, all animals were necropsied and inguinal lymph node, mesenteric lymph node, tonsil and lung were sampled for the detection of PCV-2 nucleic acid. After vaccination, all piglets were observed daily for clinical signs. Serum samples were collected on the day of vaccination and 2, 4 and 5 weeks later (at the time of necropsy). Samples were tested for presence of PCV-2 viral nucleic acid and for antibodies against PRRS and M hyo.

Results

The vaccines were safe to administer, no unacceptable side effects were seen.

The PCV-2 results showed a consistent indication of an improved protection against the PCV-2 challenge. Results are indicated in the tables 1-3 below. As can be seen, the viraemia (at SD28 and 35), but in particular the viral load in various primary tissues and the IHC score seemed to be overall improved for Group 1, the group who received the two vaccines in close proximity, i.e. within 5 cm apart, in particular around 3 cm apart.

TABLE 1

PCV2 viraemia (qPCR)

|  | Titre (log10) | | | |
|---|---|---|---|---|
|  | SD0 | SD13 | SD28 | SD35 |
| 1. PCV M HYO + PRRS (same side) | 0.00 | 0.24 | 2.10 | 1.15 |
| 2. PCV M HYO + PRRS (diff sides) | 0.00 | 0.20 | 2.38 | 1.40 |
| 3. Control (PRRS) | 0.00 | 0.65 | 4.64 | 3.28 |

TABLE 2

PCV2 viral load in tissues (log10 copies/ul)

|  | Tonsil | Lung | IngLN | MesLN |
|---|---|---|---|---|
| 1. PCV M HYO + PRRS (same side) | 4.58 | 4.42 | 3.97 | 3.86 |
| 2. PCV M HYO + PRRS (diff sides) | 5.28 | 4.77 | 4.83 | 4.06 |
| 3. Control (PRRS) | 7.41 | 6.32 | 6.71 | 6.89 |

TABLE 3

Average IHC Scores

|  | Tonsil | IngLN | MesLN | Total |
|---|---|---|---|---|
| 1. PCV M HYO + PRRS (same side) | 0.3 | 0.3 | 0.4 | 1.0 |
| 2. PCV M HYO + PRRS (diff sides) | 0.7 | 0.4 | 0.4 | 1.5 |
| 3. Control (PRRS) | 2.5 | 2.3 | 2.4 | 7.2 |

Also, the Mhyo results appeared to be improved for Group 1. The results are indicated here below in tables 4 and 5. Seroconversion was sooner and the obtained S/P ratio was also consistently higher.

TABLE 4

Percentage of seroconverted animals

|  | SD0 | SD13 | SD28 | SD35 |
|---|---|---|---|---|
| 1. PCV M HYO + PRRS (same side) | 0 | 20 | 90 | 90 |
| 2. PCV M HYO + PRRS (diff sides) | 0 | 0 | 40 | 80 |
| 3. Control (PRRS) | 0 | 0 | 0 | 0 |

TABLE 5

Immune response to M Hyo

|  | S/P | | | |
|---|---|---|---|---|
|  | SD0 | SD13 | SD28 | SD35 |
| 1. PCV M HYO + PRRS (same side) | 0.04 | 0.19 | 0.86 | 1.05 |
| 2. PCV M HYO + PRRS (diff sides) | 0.07 | 0.11 | 0.57 | 0.71 |
| 3. Control (PRRS) | 0.15 | 0.08 | 0.03 | 0.01 |

Also, the PRRS results appeared to be improved for Group 1. The results are indicated here below in table 6. The obtained S/P ration was consistently higher for Group 1.

TABLE 6

Immune response to PRRS (ELISA)

|  | S/P | | | |
|---|---|---|---|---|
|  | SD0 | SD13 | SD28 | SD35 |
| 1. PCV M HYO + PRRS (same side) | 0.29 | 0.41 | 1.28 | 1.10 |
| 2. PCV M HYO + PRRS (diff sides) | 0.35 | 0.30 | 0.80 | 0.89 |
| 3. Control (PRRS) | 0.38 | 0.34 | 0.63 | 0.52 |

In short, the associated separate injection of the PCV Mhyo vaccine and the PRRS vaccine in close proximity led to an overall better immune response when compared to administering both vaccines at different sides of the neck. Given the fact that the effect was present for all types of antigen, either a subunit antigen (ORF2 protein of PCV2), a bacterin (Mhyo) or a live attenuated virus (PRRS), the exact choice of antigen appears to be non-critical. It is thus believed that at least when the first vaccine comprises immunogen of the same basic type as the exemplified, i.e. non-replicating immunogen typically inducing a humoral immune response, and the second vaccine comprises live attenuated PRRS virus, the advantages of the invention can be obtained.

The invention claimed is:

1. A method of prophylactically treating a pig against an infection with porcine circovirus type 2 (PCV2), an infection with *Mycoplasma hyopneumoniae* and an infection with PRRS virus by injecting into a tissue of the pig at a first and a second injection site respectively, an associated separate injection of a first vaccine comprising a non-replicating immunogen of porcine circo virus type 2 (PCV2) and a non-replicating immunogen of *Mycoplasma hyopneumo-niae*, and a second vaccine comprising a live attenuated porcine reproductive and respiratory syndrome (PRRS) virus; wherein the associated separate injection of the first vaccine and the second vaccine occur simultaneously, and wherein the first and second injection sites are at most 5 cm apart from each other.

2. The method of prophylactically treating of claim 1, wherein the first and second injection sites are at most 4 cm apart from each other.

3. The method of prophylactically treating of claim 2, wherein the first and second injection sites are at most 3 cm apart from each other.

4. The method of prophylactically treating of claim 1, wherein the first and second vaccine through said injection are deposited at least partly into muscular tissue of the pig.

5. The method of prophylactically treating of claim 4, wherein the first and second vaccine are injected either by a hypodermic syringe that extends into the muscular tissue or by a jet stream of the respective vaccines using a needle-less device, wherein the jet stream penetrates the skin of the pig.

6. The method of prophylactically treating of claim 1, wherein the first vaccine and the second vaccine are administered by a single dose.

7. The method of prophylactically treating of claim 1, wherein the non-replicating immunogen of PCV2 is recombinantly expressed protein encoded by the ORF2 gene of PCV2.

8. The method of prophylactically treating of claim 7, wherein the non-replicating immunogen of PCV2 is baculovirus expressed protein of PCV2.

9. The method of prophylactically treating of claim 1, wherein the non-replicating immunogen of *Mycoplasma hyopneumoniae* is a *Mycoplasma hyopneumoniae* bacterin.

\* \* \* \* \*